US009105369B2

(12) United States Patent
Koehler

(10) Patent No.: US 9,105,369 B2
(45) Date of Patent: *Aug. 11, 2015

(54) DIFFERENTIAL PHASE-CONTRAST IMAGING WITH IMPROVED SAMPLING

(75) Inventor: Thomas Koehler, Norderstedt (DE)

(73) Assignee: Koninklijke Philips N.V., Eindhoven (NL)

(*) Notice: Subject to any disclaimer, the term of this patent is extended or adjusted under 35 U.S.C. 154(b) by 102 days.

This patent is subject to a terminal disclaimer.

(21) Appl. No.: 13/819,764

(22) PCT Filed: Aug. 26, 2011

(86) PCT No.: PCT/IB2011/053750
§ 371 (c)(1),
(2), (4) Date: Feb. 28, 2013

(87) PCT Pub. No.: WO2012/029005
PCT Pub. Date: Mar. 8, 2012

(65) Prior Publication Data
US 2013/0170618 A1 Jul. 4, 2013

(30) Foreign Application Priority Data

Sep. 3, 2010 (EP) .................................... 10175176

(51) Int. Cl.
A61B 6/00 (2006.01)
G21K 1/06 (2006.01)
(Continued)

(52) U.S. Cl.
CPC ............. *G21K 1/067* (2013.01); *A61B 6/032* (2013.01); *A61B 6/4035* (2013.01);
(Continued)

(58) Field of Classification Search
CPC ........ A61B 6/4291; A61B 6/44; A61B 6/484; A61B 6/502; G21K 2207/005
See application file for complete search history.

(56) References Cited

U.S. PATENT DOCUMENTS 5,812,629 A * 9/1998 Clauser ........................... 378/62
2007/0183583 A1 8/2007 Baumann et al.
(Continued)

FOREIGN PATENT DOCUMENTS

WO 2009113726 A2 9/2009

OTHER PUBLICATIONS

Tim Weitkamp, Ana Diaz, Christian David. "X-ray phase imaging with a grating interferometer." Optics Express 6304. Aug. 8, 2005, vol. 13, No. 16.
(Continued)

Primary Examiner — Thomas R Artman

(57) ABSTRACT

The present invention relates to differential phase-contrast imaging of an object. For increasing spatial resolution of an X-ray imaging system (2) the size of a detector pixel element (8) may be considered a limiting factor. Accordingly, it may be beneficial to increase the resolution of an apparatus (38) for phase-contrast imaging without further reducing the area of an individual pixel element (8). Accordingly, an apparatus (38) for phase-contrast imaging with improved sampling is provided, comprising an X-ray source (4), a first grating element $G_1$ (24), a second grating element $G_2$ (26) and an X-ray detector element (6) comprising a plurality of detector pixel elements (8), each detector pixel element (8) having a pixel area A. An object to be imagined (14) is arrangeable between the X-ray source (4) and the X-ray detector element (6). The first grating element $G_1$ (24) as well as the second grating element $G_2$ (26) are arrangeable between the X-ray source (4) and the X-ray detector element (6). The X-ray source (4), the first grating element $G_1$ (24), the second grating element $G_2$ (26) and the X-ray detector (6) are operatively coupled for acquisition of a phase-contrast image of the object (14). At least one of the first grating element $G_1$ (24) and the second grating element $G_2$ (26) comprise a first area $A_1$ having a first grating pitch $p_1$ and a second area $A_2$ having a second grating pitch $p_2$ different from the first grating pitch.

25 Claims, 3 Drawing Sheets

(51) Int. Cl.
*A61B 6/03* (2006.01)
*G21K 1/02* (2006.01)
*G01N 23/04* (2006.01)

(52) U.S. Cl.
CPC ............. *A61B 6/4291* (2013.01); *A61B 6/484* (2013.01); *G01N 23/04* (2013.01); *G21K 1/02* (2013.01); *G21K 2207/005* (2013.01)

(56) References Cited

U.S. PATENT DOCUMENTS

| | | | |
|---|---|---|---|
| 2010/0091947 A1* | 4/2010 | Niu et al. | 378/63 |
| 2010/0322380 A1* | 12/2010 | Baeumer et al. | 378/62 |
| 2012/0181427 A1* | 7/2012 | Kaneko | 250/336.1 |
| 2012/0189101 A1* | 7/2012 | Kaneko | 378/62 |
| 2012/0201349 A1* | 8/2012 | Kaneko et al. | 378/62 |
| 2012/0307976 A1* | 12/2012 | Kaneko | 378/62 |
| 2013/0170618 A1* | 7/2013 | Koehler | 378/62 |
| 2013/0208864 A1* | 8/2013 | Rossl | 378/62 |

OTHER PUBLICATIONS

Peter Bartl, Jurgen Durst, Wilhelm Haas, Eckhard Hempel, Thilo Michel, Andre Ritter, Thomas Weber, Gisela Anton. "Simulation of X-ray phase-contrast computed tomography of a medical phantom comprising particle and wave contributions." Proc of SPIE, vol. 7622, 76220Q-1.

* cited by examiner

DIFFERENTIAL PHASE-CONTRAST IMAGING WITH IMPROVED SAMPLING

FIELD OF THE INVENTION

The present invention relates to X-ray imaging technology in general.

More particularly, the present invention relates to differential phase-contrast imaging.

In particular, the present invention relates to an apparatus for phase-contrast imaging with improved sampling, an X-ray system comprising an apparatus according to the present invention as well as the use of an apparatus according to the present invention in one of an X-ray system and a CT system.

BACKGROUND OF THE INVENTION

When acquiring an X-ray image, an object to be examined, e.g. a patient, is arranged between an X-ray generating device and an X-ray detector. X-ray radiation emanating from the X-ray generating device is penetrating the object to be examined, subsequently arriving at the X-ray detector. The object to be examined, situated in the path of the X-ray radiation is spatially attenuating the X-ray beam, depending on the specific tissue structure within the object. The X-ray detector is subsequently detecting the spatially attenuated X-ray radiation by determining an intensity distribution of the X-ray radiation, which image information is employed for generating, further processing, and subsequently displaying an X-ray image of the object to be examined.

However, an object to be examined may provide only minor differences when attenuating the X-ray radiation, resulting in a relatively uniformly attenuated X-ray image having low contrast, thus lacking detail of the imaged inner structure of the object.

While certain objects or regions within an object may comprise similar attenuation properties, a phase of X-ray radiation penetrating the object may be influenced to a larger extent by the structure of the object.

In phase-contrast imaging, at least partly spatially coherent X-ray radiation is employed, e.g., generated by a source grating arranged adjacent to, in the vicinity of an X-ray source, e.g. an X-ray tube. Coherent X-rays penetrating the object may allow for subsequent retrieval of phase information.

However, a phase of a wave may not be measured directly, rather a phase-shift may be required to be converted to an intensity modulation, e.g., by interfering two or more waves.

For generating an according interference pattern, a so-called phase grating is employed, arranged between the object to be examined and an X-ray detector. However, an interference pattern generated by only employing a phase grating may be too small to be detectable with a current X-ray detector, due to a lack of spatial resolution of the X-ray detector.

Thus, a further analyzer grating may be employed arranged between the phase grating and the X-ray detector, subsequently providing an interference pattern, which is large enough to be detectable by current X-ray detectors.

To obtain appropriate image information, a so-called phase stepping is performed. In phase stepping, one of the source grating, the phase grating, and the analyzer grating is displaced laterally with respect to the other grating and the X-ray detector element by a fraction of its grating pitch, e.g., a fourth, sixth, eighth of the grating pitch, e.g. of the phase grating. If the phase stepping is performed using a particular grating, then the phase stepping shall cover a full period of this particular grating.

The spatial resolution of a grating based differential phase-contrast imaging system is typically limited by the size of the focal spot of the X-ray source and the size of a single detector pixel element.

While differential phase-contrast imaging may provide enhanced image information over transmission X-ray imaging taking into account attenuation only, the spatial resolution of the so obtained image information may be considered to still be limited by the individual detector pixel elements and their respective size.

Thus, for obtaining image information with increased detail, an improved or enhanced spatial resolution of acquired image information of a differential phase-contrast projection may be beneficial.

X-ray phase-contrast imaging is described in both Weitkamp T., Diaz A., David C. et al.: "X-ray phase imaging with a grating interferometer"; Optics Express 6296, 8. August 2005, Vol. 13, No. 16 as well as Bartl P., Durst J., Haas W. et al. "Simulation of X-ray phase-contrast computed tomography of a medical phantom comprising particle and wave contributions", Proc of SPIE, Volume 7622, 76220Q-1.

SUMMARY OF THE INVENTION

An aspect of the present invention may be seen as providing means for overcoming the limit of spatial resolution directly depending on the physical size of a detector pixel element, thus increasing spatial resolution beyond the actual size of the detector pixel element. This may allow improving the spatial resolution of the differential phase-contrast projection while employing a current X-ray detector or while maintaining the spatial resolution of the differential phase-contrast projection relaxing the requirements of the spatial resolution of the detector, e.g., by increasing the individual pixel area of an individual detector pixel element.

Accordingly, an apparatus for phase-contrast imaging with improved sampling, an X-ray system comprising an apparatus according to the present invention as well as the use of an apparatus according to the present invention in at least one of an X-ray system and a CT system according to the independent claims is provided.

Preferred embodiments may be taken from the dependent claims.

In particular, it may be beneficial to increase the resolution of an apparatus for phase-contrast imaging without further reducing the area of an individual pixel element.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

The figures are not drawn to scale, however may depict qualitative proportions.

DETAILED DESCRIPTION OF EMBODIMENTS

Figure 1:
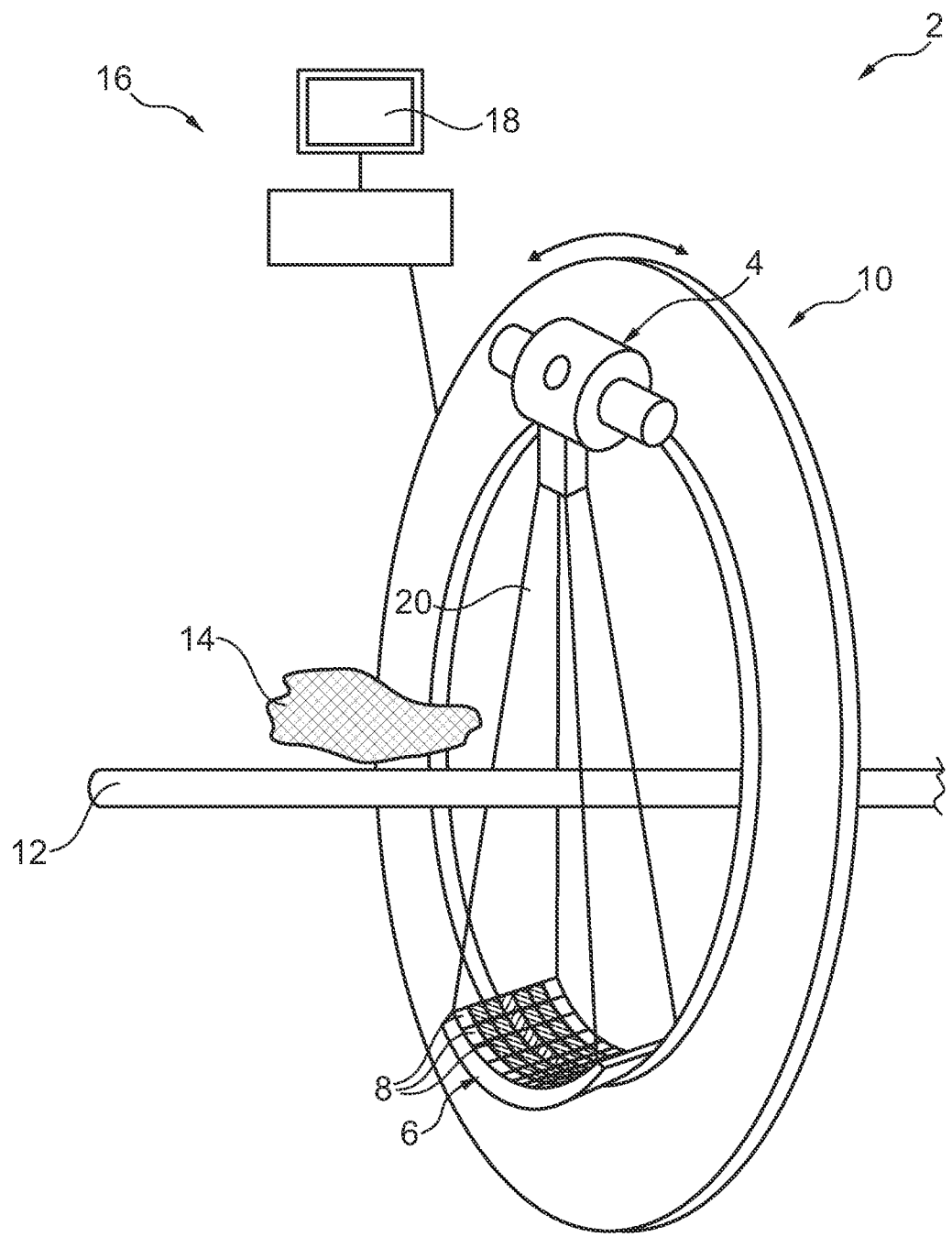
FIG. 1 shows an exemplary embodiment of an X-ray system according to the present invention.

One aspect of the present invention may be seen as employing a phase grating and an analyzer grating having a non-uniform or varying pitch structure with regard to each detector pixel. In particular, each of the phase grating and the analyzer grating may be seen as being divided in two individual areas with each individual area corresponding to the area and/or size of a single detector pixel element of the X-ray detector.

Within each area corresponding to a single detector pixel element, the grating structure of the phase grating and the analyzer grating may be a non-uniform grating structure. The non-uniform grating structure may be seen as employing at least two individual grating pitches for each detector pixel element.

The grating structure of each grating element may be seen as comprising individual barrier elements, each forming a barrier region, spaced apart from one another, thus forming a trench region between the barrier elements. Preferably, the trench region and the barrier region both comprise the same width, thus the trench region and the barrier region or barrier element are substantially of the same dimension.

The distance between two barrier elements arranged adjacent to each other may be referred to as the pitch of the grating. Thus, the pitch of a grating structure is either the width of a trench region plus the width of a barrier region or, since barrier region and trench region preferably comprise the same width, the pitch of the grating structure equals also two times either the width of a trench region or a barrier region.

A pitch of the grating may also be referred to as the periodicity of the grating.

Preferably, the area or size of the gratings corresponding to the area or size of a single detector pixel element may be halved with each half of the area corresponding to a single detector pixel element comprising an individual grating structure having an individual grating pitch. In other words, a first half of the area of one detector pixel element is covered by a grating structure having a first grating pitch and a second half of the area of one detector pixel element is covered by a grating structure having a second grating pitch, different from the first grating pitch.

In a particular embodiment, two different grating pitches $p_1$ and $p_2$ for phase grating $G_1$ may be employed each covering the respective areas $A_1, A_2$, i.e., half of the pixel area A of a single detector pixel element. A distance d between a first grating element, a phase grating $G_1$, and a second grating element, an analyzer grating $G_2$, may be exemplarily selected as the first fractional Talbot distance related to a pitch, e.g., pitch $p_1$.

The n-th fractional Talbot distance may be determined by employing the equation $$d_n = (2n-1) \cdot \frac{p_1^2}{8 \cdot \lambda} \qquad \text{Equation 1}$$

where $\lambda$ is the wavelength at a defined design energy of the X-ray source and n is a positive integer. If a spherical wave is employed, a further correction may be required, which is known in the art. Thus, the first fractional Talbot distance equals $$d_1 = \frac{p_1^2}{8 \cdot \lambda} \qquad \text{Equation 2}$$

In case the precise wavelength $\lambda$ is employed, a sharply defined interference pattern without blurring may be obtained at a fractional Talbot distance.

A second grating pitch $p_2$ may be selected to be $$p_2 = (2n-1)^{-\frac{1}{2}} \cdot p_1 \qquad \text{Equation 3}$$

Employing such a second grating pitch results in a further fractional Talbot distance relating to pitch $p_2$ to equal distance d as well. In other words, distance d is a fractional Talbot distance for pitch $p_1$ as well as a further, different fractional Talbot distance for $p_2$.

In case of equation 2 and equation 3 with n=2, distance d constitutes the first fractional Talbot distance for pitch $p_1$ as well as the third fractional Talbot distance for pitch $p_2$ at the same design energy.

Analyzer grating $G_2$ also comprises areas $A_1$ and $A_2$ having individual pitches $q_1$ and $q_2$. The respective pitches of $p_1$ and $q_1$ as well as $p_2$ and $q_2$ may be preferably related by equation 4.

$$q_i = p_i \cdot \frac{l+d}{2l}; i = 1, 2 \qquad \text{Equation 4}$$

Each individual area $A_1, A_2$ may be considered to create an individual virtual pixel on the physical detector pixel element.

If now phase stepping is conducted, the intensity variation on the first virtual pixel may be considered to comprise the period of pitch $p_1$, whereas the intensity variation of the second virtual pixel comprise the period of pitch $p_2$. Thus, the phase gradients of the respective two virtual pixels may be seen as being coded at different frequencies and thus they may both be retrieved from phase stepping. However, the minimum number of projections acquired during the phase stepping phase may have to be increased for allowing obtaining the independent parameters required for both virtual pixels.

E.g., with two different grating pitches $p_1$ and $p_2$ the minimum number of projections may to be required to be increased from three different phase stepping states to five phase stepping states. In other words, when employing a single pitch only, three individual alignment positions of the phase grating $G_1$ and the analyzer grating $G_2$ relative to one another may be considered sufficient for obtaining image information, while, when employing two different grating pitches five independent projections may have to be acquired.

Exemplarily, the intensity modulation in area $A_1$ may be modeled by the following equation.

$$I_1 = C_1 + V_1 \cdot \cos\left(\frac{2 \cdot \pi \cdot x}{p_1} + \varphi_1\right) \qquad \text{Equation 5}$$

where x is the displacement of phase grating $G_1$ and the phase $\varphi_1$ is related to the mean gradient $\partial\Phi/\partial x(A_1)$ of the x-ray wave front in the area $A_1$ according to the following equation. Furthermore, $C_1$ is related to the mean intensity during the phase stepping, which quantity relates to a conventional X-ray transmission image. $V_1$ is related to the so-called visibility function, which is affected by the bandwidth of the X-ray source, the spatial coherence of the X-ray beam, the scattering in the object and other effects.

$$\varphi_1 = \left(\frac{l \cdot d}{q_1}\right) \cdot \partial \Phi / \partial x(A_1) \qquad \text{Equation 6}$$

Correspondingly, the intensity modulation in the area $A_2$ can be modeled by the following equation $$I_2 = C_2 + V_2 \cdot \cos\left(\frac{2 \cdot \pi \cdot x}{p_2} + \varphi_2\right) \qquad \text{Equation 7}$$

with $$\varphi_2 = \left(\frac{l \cdot d}{q_2}\right) \cdot \partial \Phi / \partial x(A_2)$$

Subsequently, the total intensity measured by the individual detector pixel element may be taken from the following equation.

$$I = I_1 + I_2 \qquad \text{Equation 8}$$
$$= (C_1 + C_2) + V_1 \cdot \cos\left(\frac{2 \cdot \pi \cdot x}{p_1} + \varphi_1\right) + V_2 \cdot \cos\left(\frac{2 \cdot \pi \cdot x}{p_2} + \varphi_2\right)$$

The two phase gradients of interest $\partial \Phi / \partial x(A_1)$, $\partial \Phi / \partial x(A_2)$ may thus be obtained during phase stepping because they are coded in different frequencies $1/p_1$ and $1/p_2$. In order to retrieve the two phase gradients from the phase stepping, the grating $G_1$ should be moved now at least over the larger length of $p_1$ and $p_2$.

The concept of the present invention may not be restricted to the partitioning of the physical pixel element into two virtual pixels only. Rather by employing further different grating pitches, e.g., three different grating pitches within the area of a single detector pixel element, e.g., three virtual pixels may be generated. In such a case, seven individual projections may be required to be acquired. Accordingly, it may be beneficial that distance d equals a distance of a certain fractional Talbot distance or all grating pitches $p_1, p_2, p_3, \ldots p_n$ employed, while the number of individual images required to be acquired for reconstructing the plurality of virtual pixels it may be 2n+1.

Furthermore, it is also conceivable to select different fractional Talbot distances for the virtual pixels. In particular, distance d may also be for example the third fractional Talbot distance for pitch $p_1$ and e.g., the fifth fractional Talbot distance for pitch $p_2$. However, the sensitivity of the system to phase gradients may be seen as increasing linearly with the fractional Talbot order. In order to achieve a similar sensitivity for the different virtual pixels, it may be beneficial to employ similar fractional Talbot orders for different virtual pixels.

Now referring to FIG. 1, an exemplary embodiment of an X-ray system according to the present invention is depicted.

In FIG. 1, X-ray system 2 exemplarily is depicted as a CT system 2 comprising an X-ray source 4 and an X-ray detector 6 mounted on a gantry 10 to allow rotation of both the X-ray detector 6 and the X-ray source 4 about an axis.

X-ray source 4 generates X-ray radiation 20 emanating from X-ray source 4 and subsequently arriving at X-ray detector 6.

A support 12 is arranged within the gantry 10 of the CT system 2 for supporting an object 14 to be examined. Object 14 is arrangeable in the path of X-ray radiation 20 to allow acquisition of X-ray image information by X-ray detector 6 by its individual detector pixel elements 8. X-ray detector 6 is displayed exemplarily as a two-dimensional array of detector pixel elements 8.

A control system 16 comprising a display 18 is communicatively coupled to X-ray system 2 for controlling the image acquisition process and also for providing means for a subsequent display of acquired and reconstructed image information on display 18.

Individual grating elements for differential phase-contrast imaging acquisition are not depicted in FIG. 1. However, a detailed illustration of the path of X-ray radiation 20 from X-ray tube 4 to detector element 6 may be taken from FIG. 2.

Figure 2:
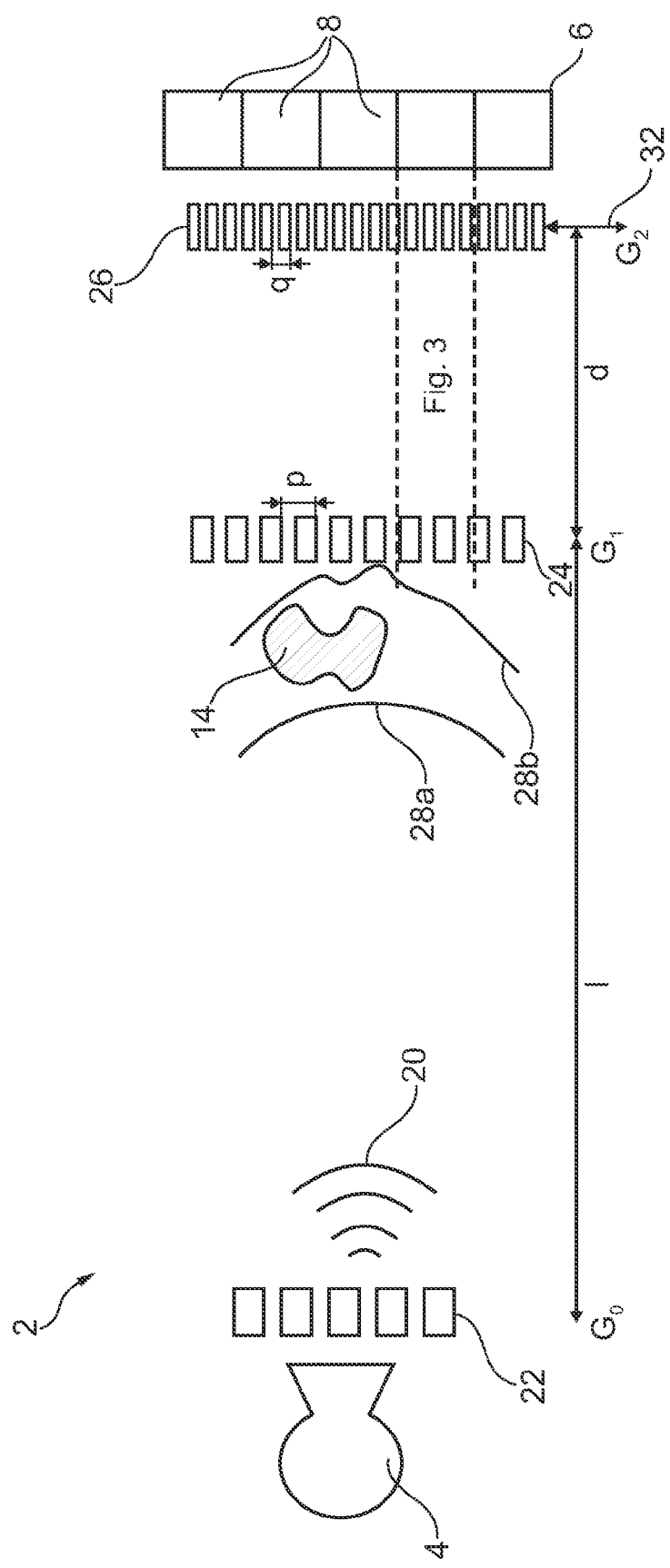
FIG. 2 shows an exemplary detail of an arrangement for phase contrast imaging according to the present invention.

Now referring to FIG. 2, an exemplary embodiment of an arrangement for phase contrast imaging according to the present invention is depicted.

In arrangement 38, X-ray source 4 is arranged in the vicinity of a source grating 22 for generating at least partially spatial coherent X-ray radiation 20. Source grating 22 is spaced apart from phase grating $G_1$ 24 by distance l. Object 14 is arranged in the path of X-ray radiation 20 between X-ray source 4 and phase grating $G_1$ 24. Wave front 28a having a uniform phase is depicted as arriving at object 14 while a further phase front 28b having a changed phase relationship within the wave front due to a phase shift imposed on the wave front while penetrating the object 14 is depicted.

Subsequently, wave fronts arrive at phase grating $G_1$ 24, which is arranged spaced apart by distance d from analyzer grating 26. Distance d may be a fractional Talbot distance for grating pitch p.

Analyzer grating $G_2$ 26 is displaceable 32 relative to phase grating $G_1$ 24 for acquisition of phase-contrast images. However it is also conceivable to displace the source grating $G_0$ 22 or phase grating $G_1$ 24 instead of analyzer grating $G_2$ 26.

X-ray radiation 20 passing through phase grating $G_1$ 24 and analyzer grating $G_2$ 26 subsequently generates an interference pattern on X-ray detector element 6 which is detectably by detector pixel elements 8.

For sake of clarity in FIG. 2, phase grating $G_1$ 24 is depicted having a uniform pitch p and analyzer grating $G_2$ 26 is depicted having a uniform pitch q. However, the detailed illustration regarding the individual pitch arrangements of both the phase grating $G_1$ 24 as well as the analyzer grating $G_2$ 26 may be taken from FIG. 3.

Figure 3:
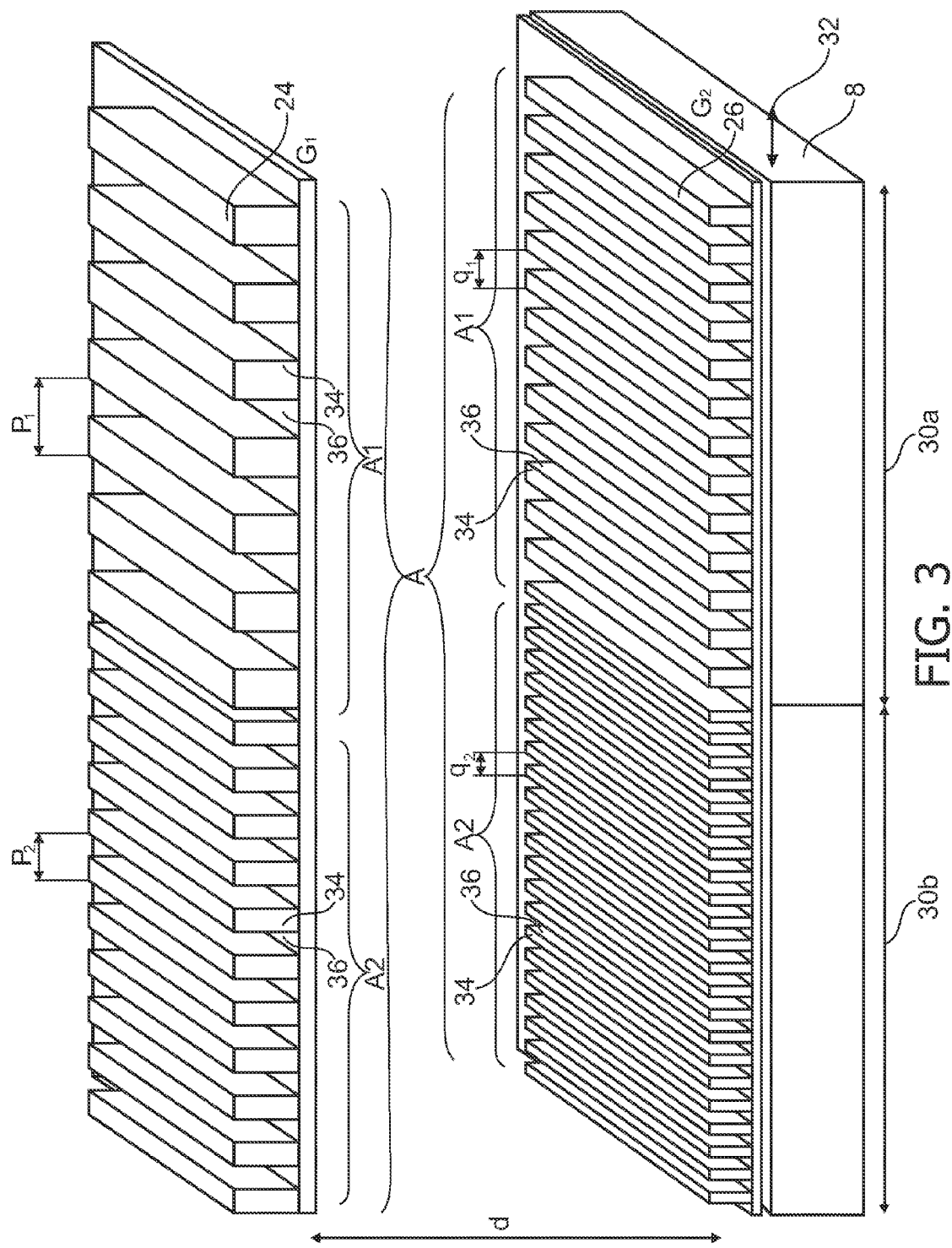
FIG. 3 shows an exemplary detail of a grating arrangement according to the present invention.

Now referring to FIG. 3, an exemplary detail of a grating arrangement according to the present invention is depicted.

In FIG. 3 in grating arrangement 40, area A of a single detector pixel element 8 as well as correspondingly sized phase grating $G_1$ 24 as well as analyzer grating $G_2$ 26 are depicted. It is to be understood that the depicted arrangement of FIG. 3 may in particular be repeated for every single detector pixel element 8 of X-ray detector 6.

Area A of detector pixel element 8 is divided into two similarly sized areas $A_1$ and $A_2$, corresponding to areas of different pitch with regard to phase grating $G_1$ 24 as well as analyzer grating $G_2$ 26. In particular, $A=A_1+A_2$.

In area $A_1$, phase grating $G_1$ 24 comprises pitch $p_1$ and analyzer grating $G_2$ 26 comprises pitch $q_1$ while in area $A_2$ phase grating $G_1$ 24 comprises pitch $p_2$ and analyzer grating $G_2$ 26 comprises pitch $q_2$.

The size and dimension of the respective pitches $p_1$, $p_2$, $q_1$, $q_2$ may be determined and set according to the foregoing description. E.g., $p_1$ and $p_2$ may be related by $$p_2 = 3^{-\frac{1}{2}} \cdot p_1$$

while $p_1$ and $q_1$ may be related by $$q_i = p_i \cdot \frac{l+d}{2l}.$$

Each grating comprises barrier elements or barrier regions 34 with intermediate trench regions 36, which may be considered to constitute gaps between the barrier elements or barrier regions 34. Each barrier region 24 and trench region 36 comprises half of the respective pitch $p_1$, $p_2$, $q_1$, $q_2$, depending on which area the respective barrier region 24 and trench region 36 is arranged in.

While with regard to phase grating $G_1$ 24, the trench regions 36 may be substantially a space or gap between adjacent barrier regions 34, the trench regions 36 of the analyzer grating $G_2$ 26 may be filled with a material, e.g., gold by electroplating.

Barrier region 34 as well as trench region 36 may be of equal width, both constituting and adding up to the respective pitch of the respective area $A_1$, $A_2$ of the phase grating $G_1$ 24 and the analyzer grating $G_2$ 26.

Exemplarily, the analyzer grating 26 may be displaceable 32 parallel to the phase grating $G_1$ 24 for conducting phase stepping. Depending on the current phase stepping state, an interference pattern may be projected onto detector pixel element 8 either in the area of virtual pixel 1 30a or virtual pixel 2 30b. Since both virtual pixels 30a,b are arranged on the same detector pixel element 8, both virtual pixels are also read out via the same physical detector pixel element 8. The detector element 6 may thus not be required to be altered.

Subsequently, the acquired image information may be sorted with regard to an individual phase stepping state, i.e., with regard to whether an acquired image information is considered to belong to virtual pixel 1 30a or virtual pixel 2 30b. Thus, image information that is to be reconstructed by the plurality of readout values of the individual detector pixel elements 8 taken into account virtual pixels 30a,b may have a spatial resolution, at least in the direction perpendicular to the grating structure, i.e., perpendicular to the barrier regions 34 and trench regions 36, that is double the spatial resolution of the detector element 6 itself.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

LIST OF REFERENCE SIGNS

2 X-ray system
4 X-ray source
6 X-ray detector element
8 Detector pixel element
10 Gantry
12 Support
14 Object
16 Control system
18 Display
20 X-ray radiation
22 Source grating
24 Phase grating $G_1$
26 Analyzer grating $G_2$
28a,b Wave front
30a,b Virtual pixel
32 Displacement/phase stepping
34 Barrier element/barrier region
36 Trench region
38 Apparatus for phase contrast imaging
40 Grating arrangement

The invention claimed is:

1. A grating arrangement for phase contrast imaging, comprising:
   a first grating element; and
   a second grating element;
   wherein at least one of the first grating element and the second grating element comprises a first area having a first grating pitch and a second area having a second grating pitch different from the first grating pitch, and
   wherein the sum of the first area and the second area corresponds to the area of a single detector pixel element.

2. The grating arrangement according to claim 1, further comprising an X-ray detector element, comprising a plurality of detector pixel elements, each detector pixel element having, as said area of a single detector pixel element, a pixel area; wherein, for a grating from among said at least one, said first area and said second area are arranged adjacently; and wherein the adjacently arranged first area and second area are collectively of a size that corresponds to said pixel area.

3. The grating arrangement according to claim 1, wherein the first area and the second area are of similar size.

4. The grating arrangement according to claim 1, wherein, for each pixel element as said single detector pixel element, said first area and said second area are, for a grating from among said at least one, defined in accordance with claim 1.

5. The grating of claim 4, the definition applying to each grating from among said at least one of the first grating element and the second grating element.

6. An apparatus for phase contrast imaging, comprising an X-ray source; and a grating arrangement according to claim 1; wherein an object to be imaged is arrangeable between the X-ray source and the X-ray detector element; wherein the first grating element and the second grating element are arrangeable between the X-ray source and the X-ray detector element; wherein the X-ray source, the first grating element, the second grating element and the X-ray detector element are operatively coupled for acquisition of a phase contrast image of the object.

7. An apparatus according to claim 6, wherein the X-ray source is configured to emit X-ray radiation having a design energy level with a defined wave length; wherein the first grating element and the second grating element are spaced apart by a distance that corresponds to a fractional Talbot distance of, for a given grating element from among the first and second grating elements, one of the first grating pitch and the second grating pitch of the defined wave length.

8. An apparatus according to claim 7; wherein said distance corresponds to a fractional Talbot distance for both the respective first grating pitch and the respective second grating pitch.

9. An apparatus according to claim 7; wherein, for said given grating element, the first grating pitch $p_1$ and the second grating pitch $p_2$ relate by $p_2 = ((2m-1)/(2n-1))^{1/2}(p_1)$, wherein said distance is the $(2m-1)^{th}$ fractional Talbot distance for the first grating pitch $p_1$, and wherein said distance is the $(2n-1)^{th}$ fractional Talbot distance for the second grating pitch $p_2$.

10. An apparatus according to claim 7; wherein said distance is one of the first and third fractional Talbot distance of, for said given grating element, the first grating pitch and the third and fourth fractional Talbot distance of, for said given grating element, the second grating pitch.

11. An apparatus according to claim 6; wherein the first grating element and the second grating element are arranged substantially parallel; and wherein the first grating element and the second grating element are configured to be movable relative to one another for providing phase stepping.

12. The grating arrangement of claim 1, said phase contrast imaging using an X-ray detector comprising, as said single detector pixel element, a pixel element having an X-ray-receiving flat area that defines a dimensional extent of said element.

13. The grating arrangement of claim 1, said first area and said second area having respective sizes, said sizes being invariant with grating element from among said at least one of the first grating element and the second grating element.

14. A grating arrangement for phase contrast imaging, comprising:
a first grating element; and
a second grating element;
wherein at least one of the first grating element and the second grating element has a grating structure and is divided into a plurality of sub-structures that are respectively divided into multiple areas having respective pitches that, per sub-structure, are not all the same, said areas having respective dimensions perpendicular to the corresponding grating structure, said dimensions and pitches being invariant among the plural sub-structures.

15. The grating arrangement of claim 14, said multiple areas being of similar size.

16. An apparatus for phase contrast imaging, comprising an X-ray source; and a grating arrangement according to claim 14; wherein an object to be imaged is arrangeable between the X-ray source and the X-ray detector element; wherein the first grating element and the second grating element are arrangeable between the X-ray source and the X-ray detector element; wherein the X-ray source, the first grating element, the second grating element and the X-ray detector element are operatively coupled for acquisition of a phase contrast image of the object.

17. The apparatus of claim 14, wherein said respective pitches are, per sub-structure, different from each other.

18. The apparatus of claim 14, said multiple areas amounting to two areas.

19. The apparatus of claim 14, said multiple areas amounting to more than two areas.

20. A grating arrangement for phase contrast imaging using a detector comprising a pixel element having a radiation-receiving flat area that defines a dimensional extent of said element, said grating arrangement comprising:
a first grating element; and
a second grating element;
wherein at least one of the first grating element and the second grating element comprises a sub-structure divided into a plurality of areas having respectively different grating pitches; and
wherein the plural areas collectively correspond spatially to said area.

21. The grating arrangement according to claim 20, wherein said detector comprises an X-ray detector.

22. The grating arrangement of claim 21, said X-ray detector comprising a multiple detector pixel elements, said pixel element being among said multiple detector pixel elements, said multiple detector pixel elements being respectively divided into a plurality of areas having respectively different grating pitches, the areas of a pixel element being arranged adjacently,
wherein, for another pixel element from among said multiple detector pixel elements, the adjacently arranged areas are collectively of a size that corresponds to said flat area of said another pixel element.

23. The grating arrangement of claim 22, wherein each pixel element has a respective radiation-receiving flat area and wherein, for each pixel element from among said multiple detector pixel elements, the adjacently arranged areas are collectively of a size that corresponds to the respective flat area.

24. The grating arrangement of claim 20, said plurality of areas amounting to two areas.

25. The grating arrangement of claim 20, said plurality of areas amounting to more than two areas.

* * * * *